United States Patent
Lafon et al.

(10) Patent No.: US 10,914,955 B2
(45) Date of Patent: Feb. 9, 2021

(54) PERIPHERAL VISION IN A HUMAN-MACHINE INTERFACE

(71) Applicant: THALES, Courbevoie (FR)

(72) Inventors: Stéphanie Lafon, Merignac (FR); Alexiane Bailly, Merignac (FR); Sébastien Dotte, Merignac (FR)

(73) Assignee: THALES, Courbevoie (FR)

( * ) Notice: Subject to any disclaimer, the term of this patent is extended or adjusted under 35 U.S.C. 154(b) by 0 days.

(21) Appl. No.: 16/272,724

(22) Filed: Feb. 11, 2019

(65) Prior Publication Data
US 2019/0250408 A1    Aug. 15, 2019

(30) Foreign Application Priority Data

Feb. 12, 2018 (FR) ...................... 18 00125

(51) Int. Cl.
 *G02B 27/01* (2006.01)
 *G02B 27/00* (2006.01)
 (Continued)

(52) U.S. Cl.
 CPC ........ *G02B 27/0172* (2013.01); *A61B 3/0033* (2013.01); *A61B 3/0058* (2013.01); *A61B 3/024* (2013.01); *A61B 3/113* (2013.01); *B64D 43/02* (2013.01); *G02B 27/0093* (2013.01); *G02B 27/017* (2013.01); *G06F 3/013* (2013.01);
 (Continued)

(58) Field of Classification Search
 CPC .... B64D 43/00; B64D 43/02; G02B 27/0093; G02B 27/017; G02B 27/0172; G02B 2027/0181; G02B 2027/0185; G02B 2027/0187; G02B 2027/014; A61B 3/024; A61B 3/0033; A61B 3/0058; A61B 3/113; G06F 3/013; G06F 2203/011
 See application file for complete search history.

(56) References Cited

U.S. PATENT DOCUMENTS

| 2010/0156617 A1 | 6/2010 | Nakada et al. |
| 2010/0207877 A1* | 8/2010 | Woodard ............... G06F 3/013 345/156 |

(Continued)

FOREIGN PATENT DOCUMENTS

| FR | 3 046 225 A1 | 6/2017 |
| WO | 2017/031089 A1 | 2/2017 |

*Primary Examiner* — Yaron Cohen
(74) *Attorney, Agent, or Firm* — BakerHostetler

(57) ABSTRACT

A computer-implemented method for managing a graphical human-machine interface, includes the steps of receiving information relating to the position of the eyes and the gaze direction of a user at the interface; receiving physiological information of the user; determining a level of cognitive load on the basis of the received physiological information; adjusting the display of the interface on the basis of the gaze direction and/or of the determined level of cognitive load. Some developments describe the management of the display zones (foveal zone and peripheral zones), the selection of one or more displays, the management of the distance from the message display to the current gaze location, the management of the criticality of the messages, various graphical techniques for attracting attention, the management of the flight context in the avionic case, the management of visual density, etc. Some system aspects are described (virtual and/or augmented reality).

12 Claims, 4 Drawing Sheets

(51) Int. Cl.
*G06F 3/01* (2006.01)
*B64D 43/02* (2006.01)
*A61B 3/024* (2006.01)
*A61B 3/00* (2006.01)
*A61B 3/113* (2006.01)

(52) U.S. Cl.
CPC ............... *G02B 2027/014* (2013.01); *G02B 2027/0181* (2013.01); *G02B 2027/0185* (2013.01); *G02B 2027/0187* (2013.01); *G06F 2203/011* (2013.01)

(56) References Cited

U.S. PATENT DOCUMENTS

2016/0272340 A1  9/2016  Leland
2017/0160546 A1  6/2017  Bull et al.

* cited by examiner

PERIPHERAL VISION IN A HUMAN-MACHINE INTERFACE

CROSS-REFERENCE TO RELATED APPLICATIONS

This application claims priority to foreign French patent application No. FR 1800125, filed on Feb. 12, 2018, the disclosure of which is incorporated by reference in its entirety.

FIELD OF THE INVENTION

The invention relates to the technical field of display methods and systems in general, and more specifically to that of multimodal interfaces in an aircraft cockpit.

BACKGROUND

In the piloting cabin of a modern aircraft, the pilot receives and manipulates a large amount of information. In some circumstances (for example flight context or mission type), the pilot may be overloaded with information to the point that he does not respond to requirements communicated by the avionic systems. In some cases, the pilot may not even perceive the stimuli. Specifically, a pilot overloaded with or distracted by other tasks might not note important information that the system may present to him. In aviation history, it has happened before that a pilot, under the effect of stress, does not perceive an audio warning. The consequences may turn out to be drastic.

Moreover, human-machine interfaces are increasingly becoming more complex. For the purpose notably of security and/or aeronautical safety, there is therefore an ever-increasing need for improved management of human-machine interfaces (in the broad sense, that is to say in a multimodal manner, i.e. involving various sensor capabilities).

Existing avionic systems inform pilots of a system fault through audio warnings or specific voice messages. Additional light indicators are sometimes redundantly used. When a datalink message is received, for example coming from air traffic control, an audio signal may be broadcast in the cockpit and specialist human-machine interfaces may signal the arrival of the messages. The pilot is then able to react, notably through touch interaction with the interface devices positioned in the cockpit (for example send messages by way of a physical keyboard). These existing solutions exhibit defects or inadequacies.

The published literature on human-machine interfaces is rich, but specific aeronautical aspects remain partly untouched, at least with regard to recent aspects.

The patent document US2016272340 entitled "Aircraft-vision systems and methods for maintaining situational awareness and spatial orientation" discloses display systems and methods for maintaining situational awareness and spatial orientation of the pilot, in particular in difficult conditions. An image with visual markers is projected into a peripheral zone of the field of view, such that these markers stimulate the peripheral vision of the pilot. This approach has limitations.

There is a need for systems and methods for managing the display at the periphery of the field of vision.

SUMMARY OF THE INVENTION

The invention relates to a computer-implemented method for managing a graphical human-machine interface, comprising the steps of receiving information relating to the position of the eyes and the gaze direction of a user at the interface; receiving physiological information of the user; determining a level of cognitive load on the basis of the received physiological information; adjusting the display of the interface on the basis of the gaze direction and/or of the determined level of cognitive load. Some developments describe the management of the display zones (foveal zone and peripheral zones), the selection of one or more displays, the management of the distance from the message display to the current gaze location, the management of the criticality of the messages, various graphical techniques for attracting attention, the management of the flight context in the avionic case, the management of visual density, etc. Some system aspects are described (virtual and/or augmented reality).

Generally speaking, the examples that are provided simplify human-machine interactions and in particular relieve the pilot of tedious manipulations that are sometimes repetitive and often complex, by the same token improving his ability to concentrate on the actual piloting. These manipulations and operations often take place in emergency contexts or contexts which require a rapid reaction. The cognitive effort to be provided for driving or piloting is optimized, or, to be more precise, reallocated to cognitive tasks that are more useful with regard to the piloting objective. In other words, the technical effects linked to certain aspects of the invention correspond to a reduction in the cognitive load of the user of the human-machine interface.

The improvements and refinements according to the invention are advantageous in that they reduce the risks of human error in the context of the human-machine interaction (for example risk of deletion of critical data or of these not being taken into account, etc.). The embodiments of the invention therefore contribute to improving security and aeronautical safety (more generally of vehicle piloting).

Some embodiments make it possible to warn or to inform the pilot visually with regard to a particular event on the basis of the cognitive load to which he is subject (for example without disturbing him from his current task). By contrast, existing solutions are fixed or static in the sense that they do not take into account the cognitive load of the pilot (an audio warning may not be perceived during a high workload, for example a message or an indicator light may leave the pilot's field of view because peripheral vision may be reduced).

Moreover, some embodiments make it possible to warn or to inform the pilot visually with regard to a particular event, regardless of where he is looking. The embodiments of the invention therefore optimize the demands and the use of the pilot's field of vision.

In some advantageous embodiments, the human-machine interface according to the invention is able to be controlled partly or fully by gaze. For example, the pilot may interact with the interface without his hands and just with his gaze. He may for example respond to (confirm or deny) a question or a request from the interface. He may also initiate an action. This interaction technique is safer in that it allows the pilot to keep his hands on the aircraft controls. By contrast, the approaches known from the prior art require a minima touch interventions, even though a pilot may sometimes not be able to use his hands (for example when he is holding the controls of his aircraft).

By expanding the display methods to augmented and/or virtual reality environments, the invention allows new interaction possibilities. By contrast, the human-machine interfaces according to the avionic prior art are generally designed with respect to the (limited or even confined) display formats. New augmented or virtual interaction possibilities make it possible to redefine the human-machine interfaces themselves. For example, the user's field of view may be used optimally and more intensively. There may be actual interactive dialogue between the machine and the human, for example so as to keep a high level of attention or to optimally utilize the latter. In this case, the embodiments of the invention make it possible to increase the display surface area used or able to be used at the periphery of the field of vision, by optimizing the use of this visual zone.

In one advantageous embodiment of the invention, the best location for displaying the information is selected in real time, notably on the basis of the pilot's gaze.

In one advantageous embodiment of the invention, a mobile icon or symbol is displayed in the peripheral field of the pilot, at a distance depending on his cognitive load.

In one advantageous embodiment of the invention, the interface is able to be controlled by gaze.

BRIEF DESCRIPTION OF THE DRAWINGS

Various aspects and advantages of the invention will appear in support of the description of one preferred, but non-limiting, mode of implementation of the invention, with reference to the figures below.

DETAILED DESCRIPTION

Figure 1:
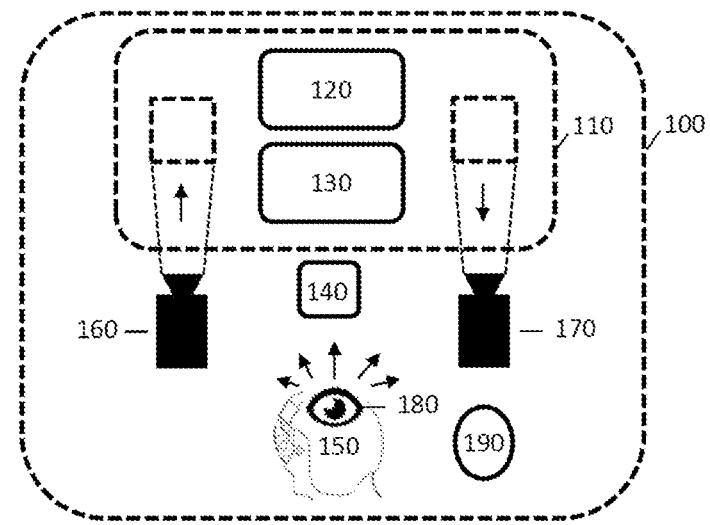
FIG. 1 illustrates an exemplary human-machine interface in the particular context of avionics, which interface is manipulated by the method according to the invention.

According to the embodiments of the invention, an aircraft may be a commercial, military or cargo aeroplane, an autonomous or remotely piloted drone, a helicopter, or any other transport means able to use a human-machine interface. The invention is not limited to aeronautical applications: the embodiments may be applicable to other types of vehicle (e.g. car, lorry, bus, train, boat, etc.).

The term "display device" manipulated by the invention denotes any display system interspersed or inserted between the visual system (i.e. the eyes) of a user (e.g. surgeon, pilot, computer scientist, etc.) and his external environment (which therefore forms a 'visual background').

The 'field of view' literally denotes the portion of space seen by an eye. An eye perceives light, colours, shapes, textures, etc. in this spatial zone. By extension, the two eyes perceive a portion of space stereoscopically. Vision may be of various types: monocular or binocular. This field of view contains several zones. The maximum acuity corresponds to the foveal zone; other zones allow reading, symbol recognition and colour discrimination. The field of vision of a driver or of a pilot changes with eye movements: for example, the field of vision decreases with speed (meaning in fact that the eyes become less mobile).

In the remainder of the document, the expression "gaze location" denotes the centre of foveal vision (centre of the zone perceived by the cone of vision).

"Peripheral" vision denotes a characteristic of human vision. With regard to foveal vision, the eye stops for 200 to 400 milliseconds on a point of fixation so as to obtain details in high resolution. Foveal vision gathers detailed but slow analysis (3 to 4 "images" per second). By contrast, peripheral vision gathers more global (or even distorted) impressions of the field of vision but that are very fast (up to 100 "images" per second). Peripheral vision therefore allows ultra-fast perception of movements. This ability to detect movements even increases towards the extreme periphery. It is estimated that peripheral vision covers more than 99% of the field of vision and is associated half and half with the optic nerve and the visual cortex.

Visual acuity is at a maximum in the foveal zone (5° FOV for "field of view", solid angle in the gaze direction). Reading is generally performed in an interval exceeding the foveal zone (10° FOV). Symbol recognition is performed in an interval of 20° FOV and discriminating colours is generally performed at an interval of 30° FOV.

Vision is said to be macular up to 18° FOV, and then beyond that vision is said to be peripheral. This peripheral vision may be broken down into "near", "mid" or "far" peripheral vision, in accordance with various thresholds (generally 60° and 120° FOV). The expression "peripheral vision" in this document denotes these various zones.

The periphery of the field of vision is relative with respect to the position of the head of the user. As the head is able to move or orientate itself (for example to the sides, upwards, downwards), it is implicit in the rest of the document that tracking the head of the pilot ("head-tracking") may be performed (if the geometric vision features require this).

The foveal zone and the peripheral vision zones fall within the (subjective) field of view, which comprises a plurality of independent or dependent components: the visual background (far environment, for example mountains, clouds, road, etc.), the displays at fixed positions in the vehicle (which may however move with respect to the position of the head of the user) and the displays worn by the user (opaque, transparent or semitransparent), which are generally attached to the head of the user.

In the embodiments in which the human-machine interface is at least partly worn (for example transparent or semitransparent virtual reality VR or augmented reality AR headset), the foveal zone and the peripheral zones move with the gaze direction. In this type of VR/AR display, the visual background (i.e. the various display planes or depths) may be modified or adjusted (in comparison with a natural and unchanging exterior on the horizon when VR or AR is not used). In other words, in this type of VR/AR environment, there are one or more (configurable and adjustable) artificial intermediate display "layers" or depths, inserted between reality and the visual system, which are able to be manipulated so as to manage this foveal zone and these peripheral zones. For example, graphical rendering (i.e. accuracy and photometric quality of images, number of polygons, latency time and graphical refreshing, etc.) may be particularly optimized for the foveal zone, whereas the peripheral zones may require less computing power. In other scenarios, the compromises may be different or even reversed.

In some embodiments, the external visual environment may be perceived transparently (in addition to a display worn by the user, elements of the cockpit instrument panel may be perceived). In other words, virtual elements as well as "real" elements may be perceived.

FIG. 1 illustrates an exemplary human-machine interface in the particular context of avionics, which interface is manipulated by the method according to the invention.

The cockpit 100 of an aircraft (or of a remote piloting cabin, or of a vehicle in the broad sense) may comprise an instrument panel 110 comprising one or more displays. A human-machine interface according to the invention may comprise a plurality of display systems, for example positioned on an instrument panel or in the cockpit and/or worn by the pilot. A display system or human-machine interface according to the invention may comprise one or more displays ("screens" or "display units") chosen from among a head-up display 120, a head-down display 130, a portable or transportable screen 140, a virtual and/or augmented reality display 150, one or more projectors 160. The human-machine interface may also comprise a camera or image acquisition device 170 and input interfaces or peripherals 180.

A head-up display 120 may be an HUD. A head-up display allows the pilot of a vehicle to monitor his environment at the same time as information supplied by his on-board instruments. This type of device superimposes particular information (e.g. piloting, navigation, mission information) in the pilot's field of vision. Various devices are known in the prior art, notably the use of projectors, of semi-transparent mirrors, of transparent projection surfaces (e.g. augmented reality) or opaque projection surfaces (e.g. virtual reality), or even projection surfaces whose opacity is able to be configured. In some embodiments, a head-up display is of binocular type (i.e. requires both eyes). In other cases, the display is of monocular type (i.e. mobilizing just one eye). In such monocular head-up systems, information is overlaid on the environment. An HUD system may therefore be monocular (for example Google Glass connected glasses), but also binocular (e.g. a "head-mounted display" or HMD system that delivers two different images, one for each eye). A display system may in some cases also be "bi-ocular" (presenting the same images to both eyes). A windscreen onto which driving information is projected provides different images to the right-hand eye and to the left-hand eye and therefore falls into the category of binocular display systems.

A head-down display 130 is a display positioned below a main zone of vision. A head-down display used by the invention may be for example a primary flight display PFD (and/or a navigation display ND/VD and/or a multifunction display MFD). More generally, the screens may be avionic flight management system screens. In the case of a land vehicle, the head-down display may for example denote an integrated GPS screen.

A portable (or transportable) screen 140 may comprise avionic screens and/or non-avionic "electronic flight bag" (or "electronic bag") means and/or augmented and/or virtual reality means.

According to the embodiments, the displays may denote or comprise virtual and/or augmented reality displays 150. Such display systems may specifically be worn by the pilot or driver. The display may therefore be individual and comprise an opaque virtual reality headset or a semitransparent augmented reality headset (or a headset with configurable transparency). The headset may therefore be a wearable computer, glasses, a helmet-mounted display, etc. The virtual or augmented reality means may denote or comprise enhanced vision system (EVS) or synthetic vision system (SVS) avionic systems.

The display in the vehicle driving or piloting cabin (the human-machine interface according to the invention) may also comprise one or more projectors 160. A projector may be for example a hand-held projector or a video projector (for example a laser projector). The information displayed for the pilot may specifically be entirely virtual (displayed in the individual headset), or else entirely real (for example projected onto the flat surfaces available in the real environment of the cockpit), or else a combination of the two (i.e. partly a virtual display overlaid on or merged with reality and partly a real display via projectors). The use of projectors makes it possible in particular to reconfigure the immersion space of the pilot (the curved surfaces of the instrument panel may be taken into account so as to create an overall merged display on demand by distorting the images that are projected). The distribution of the information projection and/or masking projection may be configurable, notably depending on the immersive visual context of the user. This "distribution" may lead to the environment being considered opportunistically by considering all of the available surfaces so as to add (superimpose, overlay) virtual information, chosen appropriately in terms of its nature (what to display), temporality (when to display, at what frequency) and location (priority of the displays, stability of the locations versus type; so as not to disorient the user, a certain consistency may be desirable). At one extreme, all of the locations that are used little or not often in the environment of the user may be utilized so as to increase the density of the display of information. The virtual/real merged display may therefore become highly fragmented (depending on the complexity of the user who is either in a white room, or in a room provided with numerous apparatuses, therefore at least a portion may be masked or hidden by the display of accepted or chosen information). Reality is therefore transformed into several "potential" screens.

All of the locations that are used little or not often in the environment of the user may be utilized so as to increase the density of the display of information. Even more, by superimposed projection of image masks on the real objects, the display is able to "erase" one or more control instruments that are physically present in the cockpit (joysticks, knobs, actuators), the geometry of which is known and stable, so as to further increase the surfaces that are able to be addressed. The real environment of the cockpit may therefore be transformed into several "potential" screens, or even into a single unified screen (configuration of reality).

Optionally, the display in the vehicle driving or piloting cabin may comprise one or more image acquisition cameras 170. A camera may be fisheye, stereoscopic or another type of camera. This feedback of images allows numerous advantageous developments of the invention. A camera or a video camera positioned in the cockpit may make it possible to capture at least some of all of the visual information displayed for the pilot (advantageously, this video feedback may be situated on a head-up visor, smart glasses or any other device worn by the pilot, so as to capture the subjective view of the pilot). Using image analysis (performed regularly at fixed intervals or continuously in the case of video capturing), the subjective view of the pilot may be analysed and modified or corrected, depending on predefined criteria and/or according to predefined objectives.

For example, in one embodiment, the visual density of the information that is displayed may be estimated. For example, this density may be estimated using various subportions of images, and display adjustments may be determined dynamically. For example, if a display screen becomes overly "burdened" (amount of text or graphical symbols exceeding one or more predefined thresholds), the lowest-priority information may be "reduced" or "condensed" or "summarized" in the form of markers or symbols. Conversely, if the density of information displayed allows, reduced or condensed or summarized information may be expanded or detailed or extended or enlarged. This management of the presentation of information may be dependent on various parameters (explained hereinafter).

The display in the vehicle driving or piloting cabin comprises one or more gaze-tracking devices 180 ("eye tracking").

The "gaze tracking" used by the method according to the invention determines the position of the eyes (origin of the vector) and the gaze direction (the vector) over time. For the sake of simplicity, the determination of the position of the eyes is implicit.

Eye-tracking (or "gaze-tracking") techniques may specifically make it possible to track ocular movements. In one embodiment, an eye-tracking system analyses images of the human eye recorded by a camera, often in infrared light, so as to calculate the direction of the pilot's gaze. In one embodiment, the variations in electrical potentials on the surface of the skin of the face are analysed. In one embodiment, the interference induced in a magnetic field by a lens is analysed. Using eye tracking, it is possible to determine the location at which the pilot's gaze is directed, and it is thus able to be determined what he is seeing (and what he is not seeing).

Various eye-tracking techniques may be used or even combined.

In one embodiment, gaze tracking is performed using an electric eye-tracking technique (Marg, 1951), by measuring differences in bioelectric potential, resulting from the bio-electric corneo-retinal field modulated by the rotations of the eye in its orbit (electro-oculograms performed with surface electrodes).

In one embodiment, gaze tracking is performed using what is called a limbus technique (Torok et al., 1951). By illuminating the limbus of the eye (separation between the sclera and the iris), the amount of reflected light depends on the relative surface area of the sclera and of the iris in the measurement field, and therefore makes it possible to identify the position of the eye.

In one embodiment, gaze tracking is performed using techniques based on the principles developed by Hirschberg in 1985. Specifically, it is possible to determine the gaze orientation by noting the position of the reflection of a light source on the cornea of the eye (corneal reflection) with respect to the pupil: a camera may detect the movement of the eye exploring an image. Quantitative analysis of the ocular movement may then be performed (number and duration of the gaze fixations, number and amplitude of the twitches, etc.). This method notably allows absolute measurements of the various positions of the eye, independently of the movements of the head of the user.

In one embodiment, gaze tracking is performed by measuring reflections of light on various structures of the eye (Purkinje images; inner and outer faces of the cornea and anterior and posterior faces of the lens). One to a plurality of cameras focused on one or both eyes make it possible to record/analyse their movements. The variants may be head-mounted ("head-mounted systems"). Other variants are non-intrusive systems. These variants may use ambient light or infrared light (for example with one or more diodes). The acquisition frequency varies between 30 and thousands of Hz. Some non-intrusive systems are calibrated.

In one embodiment, gaze tracking is performed by tracking a 3D model of the face. According to this variant, images are acquired so as to detect the face, the pupils, the mouth and the nostrils. Thereafter, a 3D model is used to evaluate the orientation of the face, and finally the gaze orientation is estimated using the images of the eyes.

In one embodiment, gaze tracking is performed using what is called the glint approach. Using the PCCR (pupil centre/corneal reflection) technique, the angle of the visual axis and the gaze location are determined by tracking the relative position of the pupil and the point of the light reflected from the cornea.

In one embodiment, gaze tracking is performed using a Tobii device (tracking of the eye at a distance using a light source close to the infrared, and then image processing using a physiological 3D model of the eye to estimate the position of the eyes and the gaze direction).

The human-machine interface according to the invention may also comprise input interfaces or peripherals 190. In one development, the device comprises means for selecting one or more portions of the virtual display. Pointing at the human-machine interfaces (HMIs) or portions of these interfaces or information may be able to be performed using various devices, for example a mouse-type pointing device or identification based on manual pointing; via acquisition interfaces (button, roller, joystick, keyboard, remote control, motion sensors, microphone, etc.), or via combined interfaces (touchscreen, force-feedback controller, gloves, etc.). The input or selection human-machine interfaces may specifically comprise one or more selection interfaces (menus, pointers, etc.), graphical interfaces, voice interfaces, gesture and position interfaces. In one advantageous embodiment, a selection may be made using gaze (for example fixation duration exceeding a threshold of predefined duration, blinking of the eye, concomitant voice command, muscle contraction, foot control, etc.). In one embodiment, a selection may be made by one or more head movements.

In one embodiment, the system knows the direction of the pilot's gaze and the position of his eyes at all times, this allowing it to select the appropriate display for displaying the messages.

The selected display may be varied (type) and a plurality of spaces or surfaces (for example planes, curves, etc.) may be mobilized. A display may be a head-down screen, an HUD, a headset visor or a windscreen. A display may also result from a projection. In some embodiments, the projection spaces are selected "opportunistically" (for example, the unused spaces of the instrument panel are used, for example the jambs or the interstitial spaces between the screens). In one embodiment, one or more spaces may be predefined for projections (they may be intentionally dedicated to this task). For example, a free zone of the cockpit may allow a projector to display information. In general, there is nothing to restrict this projection freedom, which projection may be performed onto any type of support (for example plastic, fabric, glass, etc., including a human body), given that the projection systems are able to adjust their display so as to comply with the environment and produce stable and formed images, with knowledge of the target subjective viewpoint.

Figure 2:
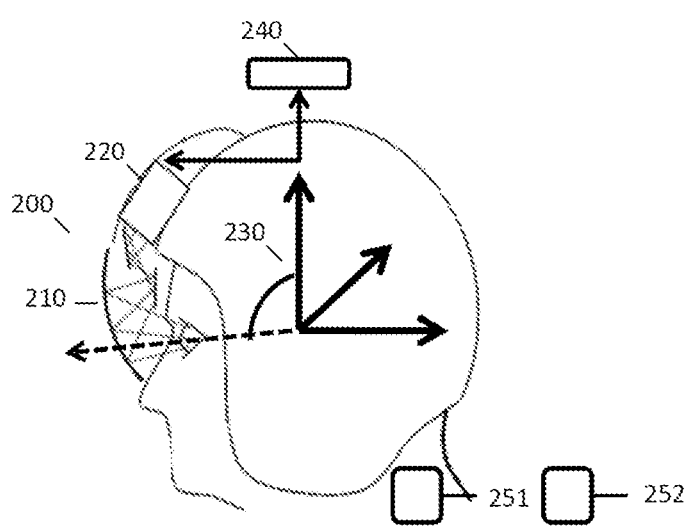
FIG. 2 illustrates a specific display system.

FIG. 2 illustrates a head-up display or HUD system 200.

The type of optional display system that is shown displays information (for example piloting information) superimposed on the external landscape (visible transparently or as captured and retransmitted in video). This display system 200 may comprise a transparent display 210 onto or on which an image is able to be projected or created, making it possible to see this image superimposed on an "external" scene. A monocular system includes a single display. A binocular system includes two displays. In some variant embodiments, the transparency of a display is variable (or configurable). A display is fixed or associated with the pilot's head, such that the display is kept close to the eye ("near-to-eye display"). In the example that is illustrated, the display is fixed to a headset worn by the pilot. Other means are possible (e.g. glasses that are worn, fixed support that the operator approaches, etc.). In some embodiments, an HUD display may be a device fixed to the aeroplane, offering a fixed field of view (generally having a 40° lateral −26° vertical field of view). In other embodiments, the head-up display is fixed to a headset or a viewing apparatus worn by the pilot. In one embodiment, one or more projectors display information on the windscreen of the vehicle (for example aeroplane or car), or else on free zones of the cockpit (for example).

This display system 200 may be associated with a system 230 for detecting the direction towards/in which the head i.e. of the operator is directed (gaze-tracking (or eye-tracking) system is used). Numerous systems allow this type of measurement (optical, electrical, mechanical etc. measurement). The system 230 maybe coupled to the display 200, but it may also be positioned elsewhere in the cockpit in the absence of a headset worn by the pilot (it may face the pilot, so as for example to measure the dilation and the direction of the pupils).

The display system 200 illustrated in the figure may comprise or be associated with a computer, i.e. computational resources 240 (e.g. computing, storage, graphics etc. resources). The computer 240 is able to control (command, manage) the projector 220. The computer may utilize the information relating to the tracking 230 of the direction of the head and/or of the gaze. It may integrate and manipulate various information relating to the aircraft and/or the mission. It determines, at each instant (continuously, according to the desired video refresh rate), the operational image to be displayed on the display.

The display system 200 may be associated with one or more human-machine interfaces (HMIs), e.g. entry peripherals (mouse, keyboard, touchscreen, touch force, haptic means, trackpad, trackball, etc.), allowing the pilot to make selections from among multiple data that are proposed, or else to enter data. According to the embodiments, the HMI may comprise various peripherals or combinations of peripherals. In some cases, voice commands may be used. In other cases, neural interfaces may be used. Interfaces for selection by eye blinking may be used.

Figure 3:
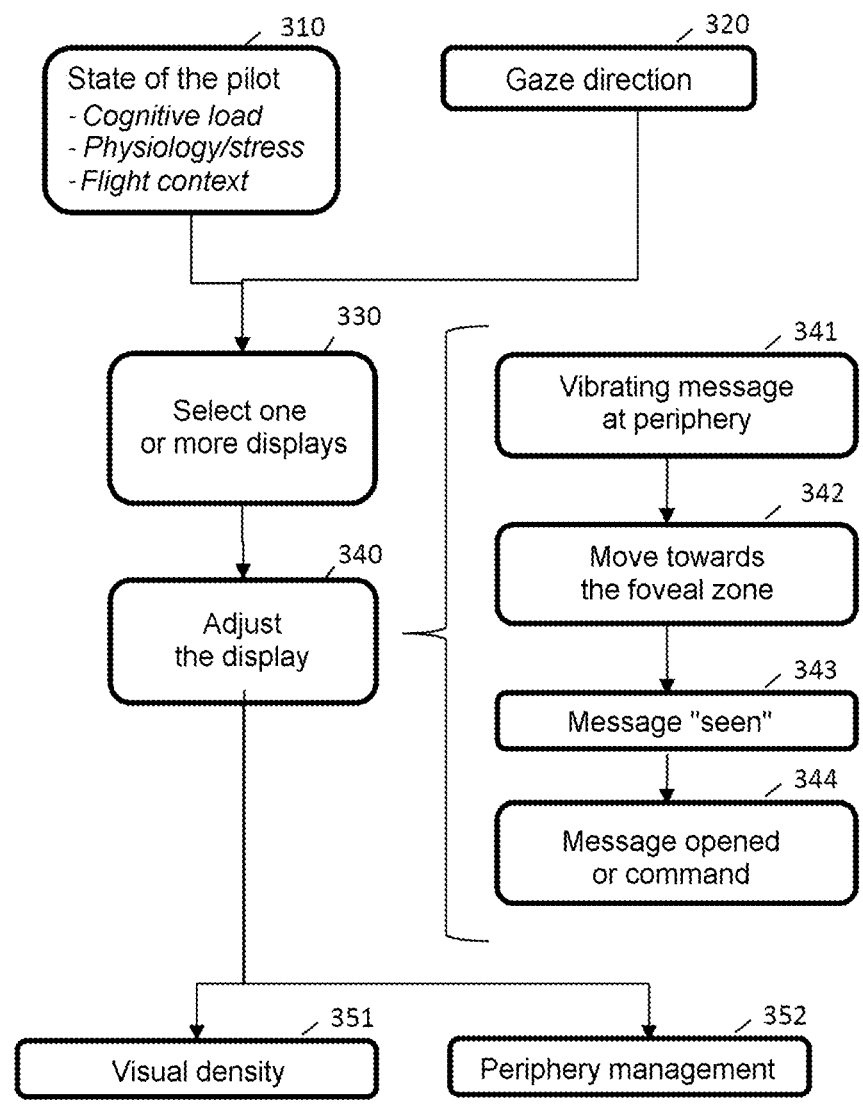
FIG. 3 shows examples of steps of the method according to the invention.

FIG. 3 illustrates examples of steps of one embodiment.

In one embodiment, there is described a computer-implemented method for managing a human-machine interface comprising a plurality of displays, the method comprising the steps of:—receiving information relating to the position of the eyes and the gaze direction of a user at the human-machine interface; —receiving physiological information of the user; —determining a level of cognitive load from among a plurality of predefined levels on the basis of the received physiological information; —adjusting the display of the human-machine interface on the basis of the gaze direction and of the determined level of cognitive load.

Monitoring the overall state of the pilot may lead to the display being adjusted or reconfigured in a certain way, for example by increasing the density of or streamlining the screens, etc. The overall state of the pilot may include various factors such as a) the cognitive load, b) the stress level correlated with the flight phase or with other events or external physical parameters such as the sound level, c) the physiological or biological parameters of the pilot, for example heart rate and perspiration giving rise to estimations of stress level. The weighting or the hierarchy between these various factors may be static or changing/dynamic, configurable or preconfigured.

In one embodiment, the method furthermore comprises a step of displaying, at the periphery of the human-machine interface, a graphical message at a configurable distance from the location of the human-machine interface at which the user's gaze is directed.

In one embodiment, the graphical message may be displayed on a plurality of displays so as to track the pilot's gaze.

In one embodiment, the graphical message may be consigned to just one and the same screen. In other embodiments, the graphical message may "change" from display to display, so as to ensure visual continuity. Like the other examples given, it may be the case that the message follows the gaze across the various displays, and is "fixed" when the pilot wishes to process it. He is then able to open an interactive interface through gaze. The message, once it has been observed or perceived, may move to its default location (trained by the pilot) so as (possibly) to be processed by him later on.

In one embodiment, the distance depends on the cognitive load and/or on the priority associated with the message. The term "priority" may be replaced with "criticality". The higher the cognitive load and/or the more critical the message, the closer it will move towards the centre of the foveal zone. This distance may also decrease over time the more critical the message becomes over the course of time.

In one embodiment, the distance decreases over time.

In some cases (critical messages), it may be intentional to request the attention of the pilot until he confirms that he has consciously accessed the information.

In one advantageous embodiment of the invention, the graphical symbol specifically follows the pilot's gaze (changing display if necessary) for as long as he has not perceived it (and therefore clearly confirmed it).

In one embodiment, the graphical message is displayed using graphical techniques comprising translational movements and/or rotations, such as vibrations, these movements and/or rotations being dependent on the content of the message.

The "content" of the message may denote its priority and/or its criticality.

Vibrations (i.e. low-amplitude movements) in peripheral vision are particularly advantageous for the reasons outlined above (properties of peripheral vision).

In one embodiment, the step of adjusting the display comprises the step of selecting one or more displays from among the displays forming the human-machine interface.

In one embodiment, the method determines the preferred display to be used on the basis of the gaze direction so as to best capture the attention of the pilot. The display closest to the foveal centre may be selected.

In one embodiment, the physiological information comprises one or more parameters comprising heart rate, heart rate variability, breathing rate, eye movements, gaze fixations, pupil dilation, cortisol level, skin temperature, skin conductivity, one or more markers of the activity of the parasympathetic nervous system, an electrocardiography signal, an electroencephalography signal, a magnetoencephalography signal, an fNIR signal or an fMRI signal.

The level of cognitive load may be determined on the basis of one or more physiological parameters of the user or of the pilot (and/or of the dynamics of these parameters), measured physically and/or estimated logically, directly or indirectly. The determination of the physiological state of the pilot may comprise direct and/or indirect measurements. The direct measurements may notably comprise one or more direct measurements of the heart rate and/or ECG (electrocardiogram) and/or EEG (electroencephalogram) and/or of the perspiration and/or of the breathing rate of the pilot. The indirect measurements may notably comprise estimations of the excitation or of the fatigue or of the stress of the pilot, which states may in particular be correlated with the flight phases or with other parameters.

The physiological parameters that are manipulated may comprise (order unimportant): gaze tracking, comprising tracking the movements of the eyes and/or the gaze fixations ("nearest neighbour index" or NRI), the cortisol level recovered in the saliva, for example ("hypothalamic pituitary adrenal" or HPA), heart rate, variability of this heart rate ("heart rate variability" or HRV), one or more markers of the activity of the parasympathetic nervous system, breathing rate, skin temperature, perspiration level, skin conductivity ("galvanic skin response" or GSR), pupil dilation ("pupilometry" or "index of cognitive activity (ICA)"), an ECG (electrocardiography) signal, an EEG (electroencephalography) signal, an MEG (magnetoencephalography) signal, an fNIR ("functional near-infrared imaging") signal or an fMRI ("functional magnetic resonance imaging") signal.

In one embodiment, the "intrinsic" or "physiological" level of mental or cognitive load is that resulting from the aggregation of physiological data measured physically and directly on the pilot. These physiological values may be weighted with respect to one another, so as to define a score between predefined limits (for example between 0 and 100), possibly able to be customized by the pilot.

This level of cognitive load may result from physiological measurements: it may "internalize" all of the internal cognitive constraints as well as the external events that are processed by the pilot's cognition. The level of cognitive load as defined is therefore necessary and sufficient to contribute to the adjustment of the display according to the invention.

In some optional embodiments, the level of cognitive load is contextualized due to external or "extrinsic" factors, such as the type of task being performed (takeoff, cruising, diversion, revision, etc.) or the flight context (noise, light, vibrations in a simulator, remote-controlled drone cabin, A380, small aeroplane, etc.). These factors considered on their own themselves may advantageously put the cognitive load of the pilot at a given time into perspective, that is to say may make it possible to determine the dynamics (for example probable change, past tendencies, etc.) therefrom. Advantageously, knowing the operating context makes it possible to anticipate, at least probabilistically, the change in the cognitive load of the pilot, and therefore the adjustments to the display intended for him.

In one embodiment, the level of cognitive load is furthermore determined on the basis of environment parameters comprising the flight context. Various tests (therefore active measurements, in addition to passive observation) may be carried out so as to evaluate the cognitive and/or physiological/biological data of the pilot. For example, the measurement of the cognitive load of the pilot may be evaluated by analysing his current behaviour regarding the ongoing piloting task (predefined criteria) and/or using additional (opportunistic, incident, etc.) tests that are optionally proposed during interstitial time intervals during which it is determined that the pilot may accept such tests. These evaluations may in turn lead to the display being adjusted.

In one embodiment, the gaze tracking determines, on the basis of predefined fixation durations and/or of predefined ocular movements, actions comprising enlarging the message, reducing the message, sending an item of data or a piloting command.

In one embodiment, the method furthermore comprises a step of acquiring at least one image of the human-machine interface.

In one embodiment, the geometry of the cockpit is known (number, types and inclines of the screens, etc.), through manual configuration or by way of a configuration file.

In one particular embodiment, the geometry of the cockpit may be known semi-automatically, or even completely automatically. For example, a "feedback" loop (for example in the form of a camera capturing the subjective visual viewpoint of the pilot) makes it possible to detect the number, the type and the configuration of each of the screens that are present (for example clipping, etc.). The step of acquiring an (overall) image of the human-machine interface is advantageous in that it allows automatic configuration of the display.

In one embodiment, the method furthermore comprises a step of measuring the visual density of the human-machine interface and the step of adjusting the display of the human-machine interface being dependent on the measured visual density.

In one embodiment, the method comprises a step of deactivating the display of the human-machine interface after the user has directed his gaze at a predefined location for a duration exceeding a predefined duration ("disengageable" graphical adjustments).

In one embodiment, there is described a system comprising means for implementing one or more of the steps of the method, the human-machine interface comprising—a plurality of displays chosen from among a head-up display 120, a head-down display 130, a portable or transportable screen 140, a virtual and/or augmented reality display 150, one or more projectors 160, a camera or image acquisition device 170; —a device for tracking the gaze of the user of the human-machine interface.

In one embodiment, the system furthermore comprises an augmented reality and/or virtual reality headset.

In one embodiment, the system furthermore comprises an adjustment feedback loop in the presence of a camera for acquiring an at least approximate image of the subjective view for the user of the human-machine interface. In one embodiment, the display is characterized by the application of predefined display rules, which depend on i) the overall state of the pilot 310 (including a weighting between a) cognitive load, b) stress level, c) ongoing activity flight phase, external environment parameters internalized in the cognitive sense) and/or on ii) the gaze direction 320.

The adjustment of the display 330 may be performed in various ways. In one embodiment, the display is modified (direct involvement). In one embodiment, the rules governing the management of the display are influenced (indirect involvement via a change in the adjustment rules).

In one development, the display in the human-machine interface is governed by predefined rules, these rules comprising display location rules and display priority rules. The map of these human-machine interfaces is defined on the basis of the real implementation configuration (simulator, aeroplane type, mission type). For example, a user (or an instructor or an airline) may manually predefine the various spatial zones in which to display a particular type of information. All or some of the screens and the associated human-machine interfaces may be transposed or moved inside a virtual or augmented reality space (where applicable). Image substitution rules or image stream rules are possible. Some rules may be associated or provide different display priorities, minimum and maximum display durations, continuous, intermittent, regular or irregular displays, optional and replaceable displays, non-deactivatable displays, display techniques or parameters (luminance, surface, texture, etc.).

In one development, the location rules are predefined. In one embodiment, the human-machine interfaces may be configured in and for a specific cockpit by the instructor depending on his personal preferences. In one embodiment, this configuration may be completely manual. For example, the instructor may provide for the display, in the headset, of windows dedicated to the instruction and that do not interfere with the vision of the students. These windows may be virtually attached to the cockpit: for example, the instructor may configure the content of these windows (parameters of the aircraft, parameters in relation to the pilots, performance monitoring, etc.). The definition of the virtual space may therefore be associated with the geometric features of the cockpit or of the flight simulator.

Generally speaking, the display of one or more symbols may be optimized (i.e. adjusted, for example to the ongoing revision and/or to the flight context). Specifically, the selected interaction model (reflected in the display of corresponding graphical symbols) may be distributed optimally over the various screens (for example spatial distribution or division of the information over the various available and/or accessible screens). For example, in terms of space, the display may be divided or broken up or distributed between a plurality of display devices where appropriate. For example, optionally, the method may graphically shift or move the whole display, for example during the input time, so as to allow the substitution model to be displayed at the limits of this display zone.

The value may for example be displayed at various locations in the field of view of the pilot, for example close to a revision means (finger, cursor) or at other locations in the cockpit (head-up projection, augmented reality superimposition, 3D rendering, etc.). In terms of time, the graphical symbol may comprise display sequences ordered in various ways.

In one embodiment, feedback (for example keyboard input) may be displayed in the peripheral field. In one embodiment, viewing the feedback is conditional on the user's gaze being fixed and/or being directed towards a certain predefined zone. According to this embodiment, a contrario, the feedback remains in the peripheral zone if the gaze path does not meet predefined conditions (for example in accordance with time and/or space criteria). In one embodiment, the feedback may "follow" the gaze, so as to remain in a state in which it is able to be called upon, but without otherwise obstructing the current gaze location.

To this end, the field of view may be "discretized" into various zones. In terms of quality, these zones may be termed (for example) frontal obstruction zone, zone for attracting high, moderate, low, zero attention, etc. In terms of quantity, the zones may be determined numerically or objectively (space perimeters, precise distances with tolerances, confidence intervals, etc.). The discretized zones of the field of view may be determined "universally" (for a group of users), or in a customized and individual manner.

In one embodiment, the visual density 341 is adjusted and/or the display in the peripheral field of vision 342 is adjusted.

The "visual density" may be manipulated. The visual density may be measured as a number of pixels switched on or active per square centimetre, and/or as a number of alphanumeric characters per unit of surface area and/or as a number of predefined geometrical patterns per unit of surface area. The visual density may also be defined, at least partly, according to physiological criteria (model of the pilot's reading speed, etc.).

In one embodiment of the invention, this visual density may be kept substantially constant. In other embodiments, the visual density will be adjusted. The flight context for example may modulate this visual density (for example, upon landing or in critical phases of the flight, the information density may be intentionally reduced or, by contrast, a maximum amount of information may be displayed).

Figure 4:
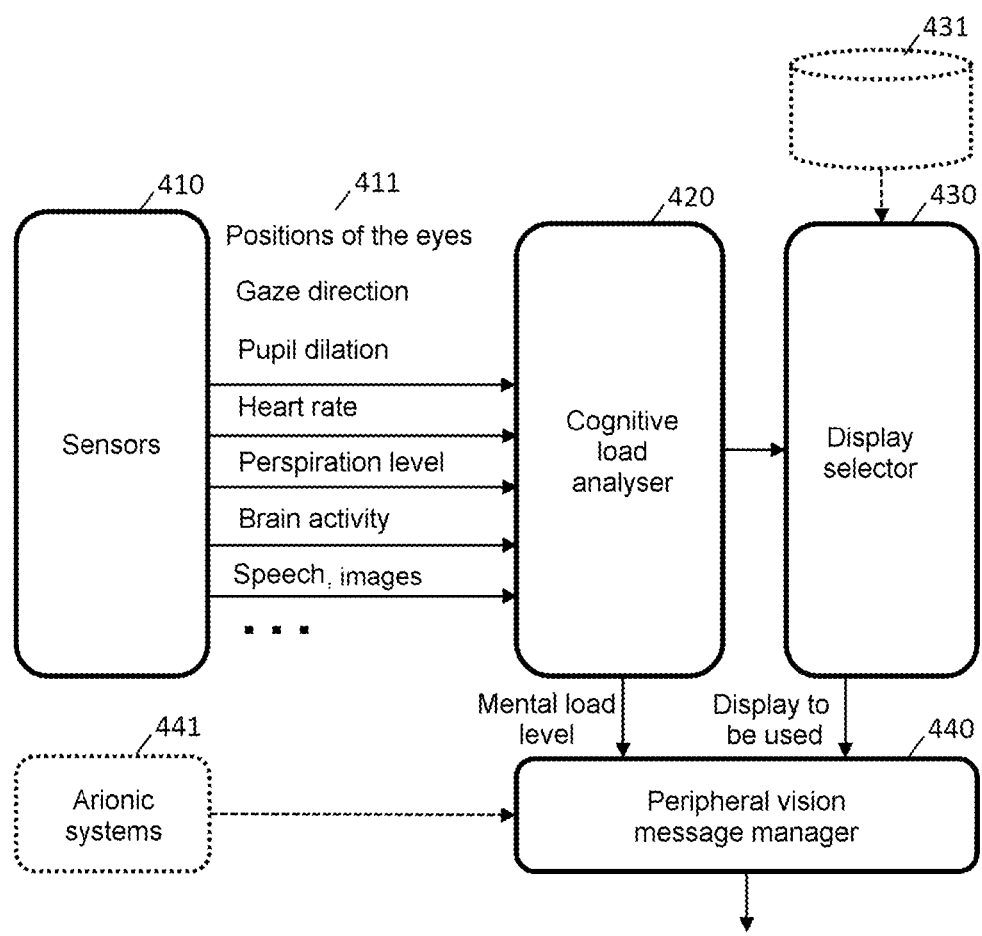
FIG. 4 describes one particular embodiment.

FIG. 4 describes one particular embodiment relating to the management of the peripheral field of vision.

The cognitive load of the pilot 420 is determined using sensors 410.

One or more parameters may determine the selection 430 of one or more displays (120, 130, 140, 150), possibly with knowledge of the geometry of the piloting cabin 431 or the available VR/AR devices.

In one embodiment, it is the gaze direction that determines the selection of the display, and not the cognitive load. The cognitive load, for its part, then determines the display distance of the messages with respect to the centre of the cone of vision.

In one embodiment, the cognitive load alone determines the selection of the display. For example, in some saturation or emergency situations, the majority of the screens may be turned off and a single screen may be mobilized (regardless of the gaze direction).

In one embodiment, both factors are involved (in equal proportions or in different weightings or compromises). The gaze direction and the cognitive load directly or indirectly influence the selection of the display (one or more displays).

Thereafter, a peripheral vision message manager 440 interacting with the avionic systems 441 displays one or more messages on the selected displays or display systems (120, 130, 140, 150, 160).

The sensors 410 are notably direct or indirect physiological sensors measuring physical or chemical parameters. The sensors 410 may notably comprise eye-tracking apparatuses (for example positions of the eyes, movements, gaze direction, pupil dilation, detection of blinking and the frequency thereof, etc.), devices for measuring physical parameters of the environment (for example ambient brightness, humidity, sound level, exhaled $CO_2$, etc.), and physiological measurement devices (for example for measuring heart rate; breathing rate; EEG; ECG; perspiration level, for example neck, hand perspiration; eye moisture; movement of the pilot's body, head, hands, feet, etc.).

The set of raw signals is centralized and analysed in a logic unit, called "cognitive load analyser" 420, which interprets and categorizes the set of measured parameters into predefined categories, notably according to discretized levels of "cognitive load" (for example "maximum cognitive load", "rapidly increasing cognitive load", "zero cognitive load (sleeping)", etc.).

The discretization of the states of cognitive load may be modulated or attenuated or qualified by numerous other additional optional parameters, for example according to stress levels that are themselves also quantified (for example "no stress" or "maximum stress (landing)". An intense cognitive load may thus occur when there is no stress or by contrast in a state of maximum stress. Moreover, the flight context may encourage or suppress stress and/or cognitive load (which differ depending on the flight phases of takeoff, climbing, cruising, diversion, flight plan revision, landing, taxiing, etc.).

The various categories thus obtained may each be associated with rules for managing the display of messages 440.

The display may be managed according to various objectives, notably attention criteria. The human brain, although it is perceiving the visual signals correctly (at the limit without the appearance of binocular rivalry), may specifically "hide" information elements in some circumstances. For example, a car driver who is concentrating completely on a passing manoeuvre may neglect a speed limit warning light, even though his visual system has decoded it perfectly and fused the visual stimuli. A pilot concentrating on an object present on the horizon may neglect objects present in the first plane, which are possibly hazardous. This attentional rivalry, which is exclusive and specific to each brain, is not able to be measured or inferred (black box'). By contrast, reminders (and variations thereof, so as to avoid accustomization) may expediently be implemented, so as to make it possible in fine to hold the attention of the user (placed in a risky situation or a scenario-based decision, justifying keeping a state of alertness or particular awareness).

According to the embodiments of the invention, all or some of the available displays will be called upon.

In one particular embodiment, a single screen is selected depending on the gaze direction. Advantageously, selecting a single screen (for example the one situated at the shortest distance from the current gaze location) allows a fast and natural interaction (in the sense that it minimizes disturbances or visual changes). One of the noteworthy advantages of the invention lies in "neglecting" the displays and tracking gaze so that the pilot is able to interact quickly.

In one particular embodiment, one or more screens ("display units", "displays") are selected depending on the determined cognitive or mental load and/or on the gaze direction.

The selection of displays 430 may be performed in various ways.

In one embodiment, the selection of displays may notably draw on the knowledge of the geometry of the piloting cabin (surface areas of the various screens, their shapes, their positions in space, the ones that are consulted most often by the pilot, where the foveal zone is, etc.). As this configuration does not change much, this initial configuration solution may be sufficient and satisfactory.

In one embodiment, this knowledge of the geometry may be determined or obtained by using subjective view image capturing (for example a video camera mounted on the headset worn by the pilot may make it possible to approximate what he is perceiving in his environment, arranged on multiple screens). Thereafter, the desired display region may be matched to a particular screen (addressing). This development provides flexibility (and does not necessarily require manual calibration).

In one particular embodiment, the display of the human-machine interface may take into account the position of the operator and/or the gaze direction, so as notably always to be presented in accordance with the geometry of the cabin or in an optimized subjective view.

In one particular embodiment, the existence of a video feedback loop may be particularly advantageous in that it may make it possible, notably coupled with the use of projectors, to dynamically redefine the visual environment of the user, for example by adapting to the environment (using automated or automatic methods).

The use in combination of the gaze-tracking device of the human-machine interface according to the invention is particularly advantageous in that it makes it possible to modulate or adjust or influence the location rules and/or display priority rules.

In some advantageous embodiments (for example in the case of a cognitive tunnel), the excessively distant screens are turned off. Some variants provide for the gradual reduction of visual density (so as to minimize disturbances with regard to the pilot).

With regard to the peripheral vision message management 440, numerous embodiments are possible.

Figure 5:
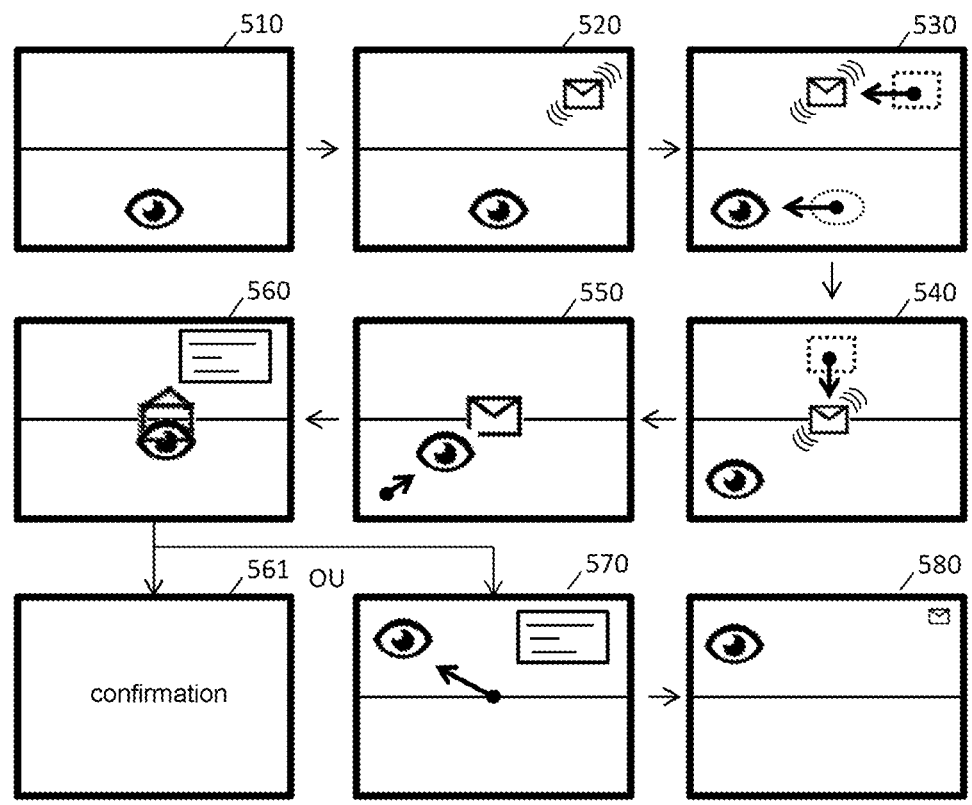
FIG. 5 illustrates an example of managing a message according to one particular embodiment of the invention.

FIG. 5 illustrates one example of managing the display in the peripheral field of vision.

With knowledge of the overall state of the pilot (internal cognition) and the external parameters (flight phase, priority of a message), the method according to the invention comprises a step of receiving a message from the avionic systems (for example weather alert, flight instruction, ATC instruction, diversion, etc.). This message may be associated with a variable level of priority or of criticality.

The method may oversee the display, on the basis of factors comprising the cognitive state of the pilot (mental load) and his gaze direction.

One embodiment that is entirely specific and that would not be limiting is described hereinafter. In step 510, the pilot's gaze is determined as being directed at a given location in the human-machine interface. In one embodiment, a message of priority exceeding a predefined threshold is broadcast by the avionics services: this message requires the short-term attention of the pilot. In another embodiment, the state of awareness of the pilot requires his attention to be maintained or regained: a specific message should stimulate the pilot.

Thereafter, in step 520, a message is displayed at the periphery. In one advantageous embodiment, this message vibrates. In one embodiment, the message vibrates using techniques that depend on the predefined criticality associated with the message (the form depends on the background). Vibrations (i.e. low-amplitude movements) in peripheral vision are particularly advantageous for the reasons outlined above (properties of peripheral vision).

In step 530, the pilot continues his activity whether or not he has (visually) perceived the message displayed at the periphery: his gaze moves. The message, rather than remaining still, moves in correlation with the gaze movement (using various techniques: proportionally, in parallel, etc.). This step 530 gradually attracts the attention of the pilot.

In step 540, the pilot is still looking elsewhere, i.e. is still not consulting the message. The display management then intentionally moves the display of the symbol/icon towards the active location of the pilot's gaze. In one embodiment, the spatial distance between the vibrating message and the gaze location may notably depend on the cognitive load of the pilot. In one embodiment, the message moves towards the foveal vision when a predefined mental load level has been reached. In one embodiment, the distance may depend on this cognitive load and on the criticality of the message. The function governing the distance may be a mathematical (analytical) function, but may also be of algorithmic type (result of a sequence of steps, not able to be formulated analytically). The function may for example reduce the distance over time. As the case may be, the reduction may be performed at a constant speed or accelerate.

In step 550, the pilot becomes aware of the message, he looks at it and "sees" it. At this time, the vibrations of the message stop. In other words, if the gaze is directed towards the message, said message becomes fixed (the vibrations disappear) so as to allow the message to be opened and processed.

Various embodiments are possible.

Several techniques exist for determining that a graphical object (such as a message) has been "seen", and more generally for controlling the human-machine interface (selecting a displayed object). These techniques may be combined.

In one embodiment, it is determined whether the path of the pilot's gaze (i.e. of its projection onto the plane or space of the human-machine interface) passes through that of a predefined zone (for example around a particular object of the interface). The zone may be strictly defined, i.e. according to strict contours, but also according to tolerance margins (for example gradual buffer zones, etc.). These margins may be associated with the measurement errors of the gaze tracking. One or more points of intersection may be determined between one or more zones of the human-machine interface and the gaze path (or simply its location) at a given time. These points of intersection may in turn trigger one or more actions (for example confirm sending of a response, other display, etc.). In one embodiment, the duration for which the pilot's gaze passes through a predefined zone associated with a message is a parameter able to be manipulated by the method according to the invention.

In one embodiment, the ocular path or gaze path crosses ("intersects", "passes through") the message; this exclusively spatial condition, which is necessary and sufficient, determines that the message has been seen. This embodiment has the advantage of not disturbing the "natural" activity of the pilot. In one embodiment, the conditions are spatial and temporal: a predefined minimum duration is required (the pilot has to remain on the message for a few fractions of a second so that said message is considered to be seen). In one embodiment, the crossing duration is at a maximum (if the gaze dwells on a given zone, a different action may be required). In one embodiment, the crossing duration should be within a predefined interval (either absolute, i.e. regardless of the message, or relative to the type of message or to its content), between a minimum duration and a maximum duration.

In step 560, the pilot's gaze is directed to the message in excess of a predetermined duration, and the message is then "opened". For example, a larger display surface is used, adjacent to the initial symbol.

Several interactions are then possible. In step 561, the pilot may look at the response to be sent and confirm it using a physical means for securing the interaction.

For example, in the aeronautical field, for critical operations such as interactions with air traffic control (ATC), such as sending a datalink message, physical or haptic confirmation may be required (by convention). For driving a partly automated land vehicle, in the same way, some physical actions may be required (for example for overtaking manoeuvres, etc.).

The pilot is also able to control—by gaze—an action preconfigured in or by the message (for example confirm a command, select from a list, close a window, confirm, deny, etc.). In another sequence, the pilot may simply ignore the message in step 570, which will then be "reduced" in step 580 (for example to a normal location or one that does not vary in space, defined by the human-machine interface). Reduction may be understood to mean that the message is miniaturized (the display surface is reduced) or that a symbol representing it is substituted for it. Other techniques are possible. Combinations of interactions are possible: for example, after confirmation 561, the message may also be reduced in the peripheral field.

In other words, receiving a request to warn or to inform the pilot, the method according to the invention may display a dedicated icon in the peripheral field of the pilot at a distance depending on the current cognitive load of the pilot (the higher this cognitive load, the closer the icon will be; this position being able to vary between 10° and 30° for example). In one embodiment, the method according to the invention may comprise a step of defining the display closest to the horizontal line associated with the current gaze location (for example a head-down screen, an HUD, the visor of a headset, the windscreen, etc.). This feature is advantageous ("seamless display"), i.e. minimizing graphical changes or surprise effects. The display may be selected for example using a database containing information on the position of the displays in the cockpit (and their shape, for example). The displayed symbol or icon may vibrate, so as to capture the attention of the pilot. A vibration or oscillation is advantageous as humans are more sensitive to movements than to shapes or colours in peripheral vision. In one embodiment, the icon may "follow" the pilot's gaze (e.g. mimicking or proportional or parallel movements). Following may be continued until a predefined duration has elapsed and/or until the pilot has seen it (for example depending on the level of criticality of the information). Once it has been "looked at", a more specific or expanded or rich or detailed interactive message may appear. The pilot may process the message later on; where applicable, the message may put itself in the position that is initially reserved for it. If the pilot effectively looks at the message, he is able to read information from it and choose to perform certain functions contained in the message, for example by looking at buttons dedicated to these actions (therefore using gaze control). The human-machine interface according to the invention may be controlled by gaze and/or physical input interfaces (e.g. buzzer, mouse, touch, voice command): the interface may be able to be controlled exclusively by gaze, or able to be controlled exclusively by physical means or else by a combination of the two types of control (i.e. gaze and physical action).

A description is given of a computer program product, said computer program comprising code instructions for performing one or more of the steps of the method when said program is executed on a computer.

By way of example of hardware architecture appropriate for implementing the invention, a device may include a communication bus to which a central processing unit (CPU) or microprocessor are connected, which processor may be "multicore" or "manycore"; a read-only memory (ROM) able to contain the programs necessary for implementing the invention; a random access memory (RAM) or cache memory containing registers suitable for recording variables and parameters that are created and modified during the execution of the abovementioned programs; and an I/O ("input/output") or communication interface suitable for transmitting and for receiving data. If the invention is implanted in a reprogrammable computing machine (for example an FPGA circuit), the corresponding program (that is to say the sequence of instructions) may be stored in or on a storage medium that is removable (for example an SD card or a mass storage means, such as a hard disk, e.g. an SSD) or that is non-removable, that is volatile or non-volatile, this storage medium being readable in part or in full by a computer or a processor. The reference to a computer program that, when it is executed, performs any one of the previously described functions is not limited to an application program being executed on a single host computer. On the contrary, the terms computer program and software are used here in a general sense to refer to any type of computer code (for example, application software, firmware, microcode, or any other form of computer instruction, such as web services or SOA or via programming interfaces API) that may be used to program one or more processors so as to implement aspects of the techniques described here. The computing means or resources may notably be distributed ("cloud computing"), possibly with or using peer-to-peer and/or virtualization technologies. The software code may be executed on any suitable processor (for example a microprocessor) or processor core or a set of processors, whether these are provided in a single computing device or distributed between several computing devices (for example such as possibly accessible in the environment of the device). Security technologies (cryptoprocessors, possibly biometric authentication, encryption, chip card, etc.) may be used.

The invention claimed is:

1. A computer-implemented method for managing a human-machine interface comprising a plurality of displays, comprising the steps of:
receiving information relating to the position of the eyes and the gaze direction of a user at the human-machine interface;
receiving physiological information of the user;
determining a level of cognitive load from among a plurality of predefined levels on the basis of the received physiological information;
adjusting the display of the human-machine interface on the basis of the gaze direction and of the determined level of cognitive load,
displaying, at the periphery of the human-machine interface, a graphical message at a configurable distance from the location of the human-machine interface at which user's gaze is directed, the distance being dependent on the cognitive load and/or on the priority associated with the message, and the distance decreasing over time.

2. The method according to claim 1, the graphical message being displayed using graphical techniques comprising translational movements and/or rotations, such as vibrations, these movements and/or rotations being dependent on the content of the message.

3. The method according to claim 1, the step of adjusting the display comprising the step of selecting one or more displays from among the displays forming the human-machine interface.

4. The method according to claim 1, the physiological information comprising one or more parameters comprising heart rate, heart rate variability, breathing rate, eye movements, gaze fixations, pupil dilation, cortisol level, skin temperature, skin conductivity, one or more markers of the activity of the parasympathetic nervous system, an electrocardiography signal, an electroencephalography signal, a magnetoencephalography signal, an fNIR signal or an fMRI signal.

5. The method according to claim 1, the level of cognitive load furthermore being determined on the basis of environment parameters comprising the flight context.

6. The method according to claim 1, the gaze tracking determining, on the basis of predefined fixation durations and/or of predefined ocular movements, actions comprising enlarging the message, reducing the message, sending an item of data or a piloting command.

7. The method according to claim 1, furthermore comprising a step of acquiring at least one image of the human-machine interface.

8. The method according to claim 1, furthermore comprising a step of measuring the visual density of the human-machine interface and the step of adjusting the display of the human-machine interface being dependent on the measured visual density.

9. A computer program product, said computer program comprising code instructions for performing the steps of the method according to claim 1, when said program is executed on a computer.

10. A system comprising means for implementing the steps of the method according to claim 1, the human-machine interface comprising
a plurality of displays chosen from among a head-up display 120, a head-down display 130, a portable or transportable screen 140, a virtual and/or augmented reality display 150, one or more projectors 160, a camera or image acquisition device 170;
a device for tracking the gaze of the user of the human-machine interface.

11. The system according to claim 10, furthermore comprising an augmented reality and/or virtual reality headset.

12. The system according to claim 10, furthermore comprising an adjustment feedback loop in the presence of a camera for acquiring an at least approximate image of the subjective view for the user of the human-machine interface.

* * * * *